United States Patent [19]

Takashi et al.

[11] Patent Number: 4,679,920
[45] Date of Patent: Jul. 14, 1987

[54] AUTOMATIC PERIMETER

[75] Inventors: Shioiri Takashi, Wako; Kobayashi Katsuhiko, Chiba; Tago Hideo, Matsudo, all of Japan

[73] Assignee: Tokyo Kogaku Kikai Kabushiki Kaisha, Tokyo, Japan

[21] Appl. No.: 703,317

[22] Filed: Feb. 20, 1985

[30] Foreign Application Priority Data

Feb. 24, 1984 [JP] Japan ................................. 59-33754
Mar. 16, 1984 [JP] Japan ................................. 59-50702

[51] Int. Cl.⁴ ............................................. A61B 3/02
[52] U.S. Cl. ................................................... 351/226
[58] Field of Search ....................... 351/224, 225, 226

[56] References Cited

U.S. PATENT DOCUMENTS 4,146,311 3/1979 Nurr ..................... 351/226
4,255,022 3/1981 Kuether et al. .
4,255,023 3/1981 House ..................... 351/226
4,260,227 4/1981 Munnerlyn .......................... 351/226

OTHER PUBLICATIONS

"An Automatic Static Perimeter, Design and Pilot Study on Acta Ophthalmologica", (vol. 53, 1975), pp. 293-310.
"Automatic Perimetry in Glaucoma Visual Screening" on Graefes Archiv Ophthalmologie, (Band 199, Heft 1, 1976) pp. 21-37.

Primary Examiner—Rodney B. Bovernick
Attorney, Agent, or Firm—Brumbaugh, Graves, Donohue & Raymond

[57] ABSTRACT

An automatic perimeter automatically presenting stimuli in a plurality of conditions, in which the presentation of stimuli can be readily stopped by an operator during the presentation, and an accurate examination of eyesight is carried out in accordance with eliminating the few latest perception signals before the stimulus presentation is stopped during an examination of eyesight.

6 Claims, 4 Drawing Figures

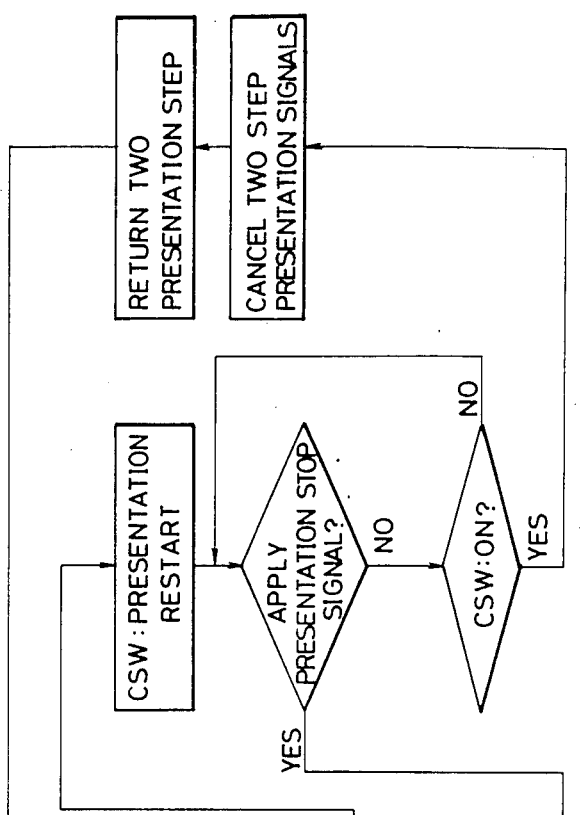
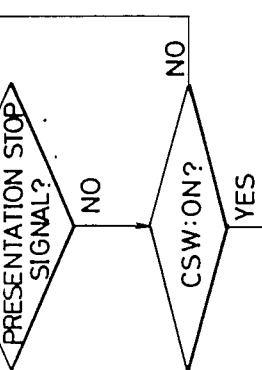
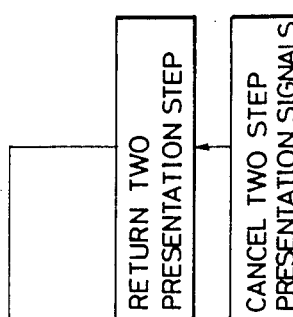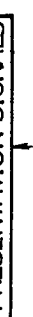
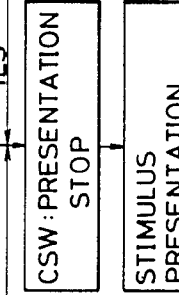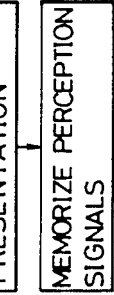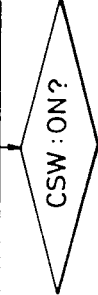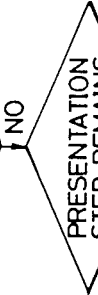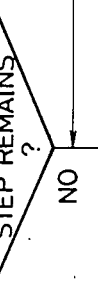
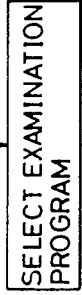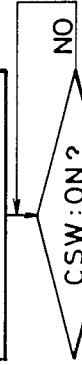
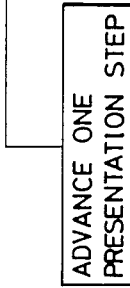
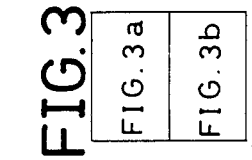
FIG. 3a
FIG. 3
| FIG. 3a |
| FIG. 3b |

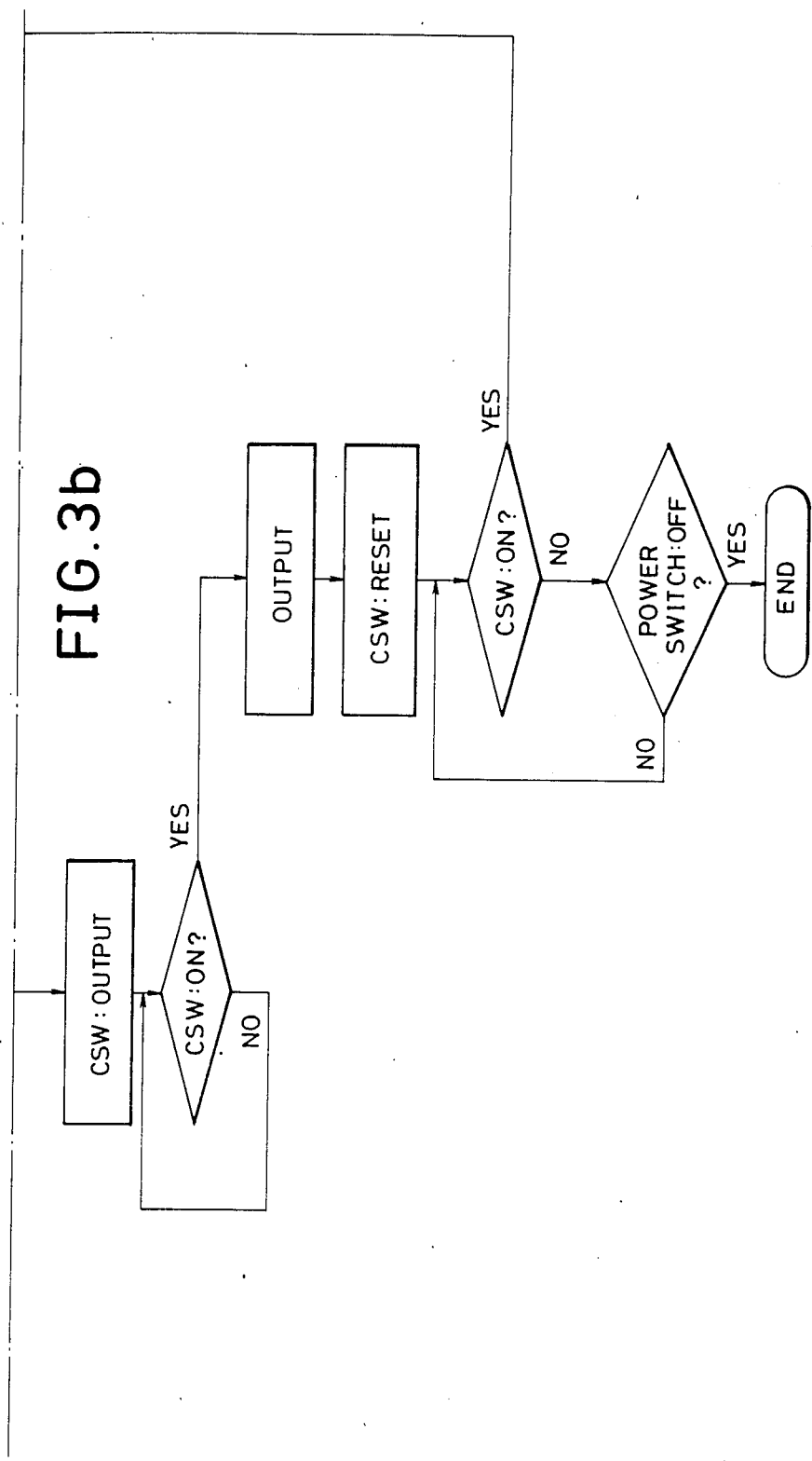

AUTOMATIC PERIMETER

BACKGROUND OF THE INVENTION

1. Field of the Invention

The present invention relates to an automatic perimeter for automatically examining the field of vision of a patient's eye. More specifically, the present invention pertains to an automatic perimeter which is designed to automatically present marks or stimuli in accordance with various conditions including brightness, positions, presentation time and presentation intervals of the marks.

2. Description of the Prior Art

In general, a perimeter has a hemispherical concave screen on which stimuli are presented. In such perimeter, a patient's eye to be examined is located at the center of the sphere of the screen and the sight axis of the eye is fixed to the center of the screen by having the eye see a fixed viewing target on the screen. Then, the stimuli are presented in accordance with various conditions in sequence at various positions on the screen with different sizes and different brightness so as to distinguish visible zone from invisible zone.

In conventional automatic perimeters, presentations of the stimuli are automatically made upon initiation of the operation in accordance with a predetermined schedule until presentations of all stimuli are completed so as to reduce a burden to the operator. It should however be noted that it may sometimes be required to stop the presentation of the stimuli. For example, when the operator finds that the sight axis is not fixed to the center of the screen, the operation must be interrupted to repeat past steps of the operation. Further, when the operator believes that he could obtain data sufficient to determine the visual field, further measuring steps may no longer be necessary. In order to make it possible to perform such control, the conventional perimeter includes manual switches or photoelectrical switches. It should however be noted that such switches are inconvenient to actuate because the examination must be carried out in a dark room, and the operator must continue to ensure that the sight axis is fixed to the center of the screen during the examination so that it is difficult to locate an appropriate switch.

Further, when it is found during an examination that the sight axis is offset from the center of the screen, there is a high possibility of errors being produced due to such offset of the sight axis in a certain number of perception data already obtained. Therefore, if presentations of the stimuli are restarted to examine the eyesight with all of the data already obtained being used for determining the viewing field, it is difficult to maintain the accuracy of the examination.

OBJECT OF THE INVENTION

It is therefore an object of the present invention to provide an automatic perimeter in which presentation of stimuli can be readily stopped by an operator during presentation.

Another object of the present invention is to provide an automatic perimeter which can perform an accurate examination of eyesight.

A further object of the present invention is to provide an automatic perimeter in which any possibility of measuring error due to an interim stop of measurement can be eliminated.

SUMMARY OF THE INVENTION

According to present invention, the above and other objects can be accomplished by an automatic perimeter comprising stimulus presentation means for presenting stimuli to a patient, presentation condition memory means for memorizing a plurality of presentation conditions, control means for controlling the stimulus presentation means so as to present the stimuli in accordance with the presentation conditions memorized in the presentation condition memory means, response means operated by the patient for supplying perception signals responding to presented stimuli, response signal memory means for memorizing the perception signals in relation to the presentation condition thereof, output means for supplying output of the perception signals memorized in the response signal memory means, first input means for applying a plurality of command signals to the control means, second input means for taking part of said first input means to apply a part of the command signals which are to be applied by the first input means, and function change means for changing the command signals generated by the second input means in response to the stimulus presentation condition controlled by the control means.

In a preferable aspect of the present invention, the first input means comprises a cathode-ray tube displaying a plurality of control commands and a light pen.

In another aspect of the present invention, the second input means comprises a manual switch.

In another aspect of the present invention, the second input means includes means to start examination before beginning presentation of stimuli and to stop and restart the presentation of stimuli.

According to a specific aspect of the present invention, there is provided an automatic perimeter comprising stimulus presentation means for presenting a plurality of stimuli in a manner wherein one of the stimuli is presented to a patient at a time, presentation condition memory means for memorizing a presentation condition on a plurality of steps, control means for supplying presentation control signals to the stimulus presentation means in accordance with the presentation condition memorized in the presentation condition memory means, response means operated by a patient for supplying perception signals responding to presented stimuli, response signal memory means for memorizing the perception signals in relation to the presentation condition thereof, output means for supplying output of the perception signals memorized in the response signal memory means, and a signal application means for supplying presentation stop signal and presentation restart signal to the control means and supplying at least one of the signals to the response signal memory means, whereby the control means stops supplying the presentation control signal to the stimulus presentation means on taking the presentation control signal, and returns a predetermined-number of presentation steps and restarts supplying the presentation control signals on taking the presentation restart signal, and the memorized perception signals in response to the returned presentation steps are canceled when the response memory means takes either the presentation stop signal or the presentation restart signal.

In a further preferable aspect of the present invention, the automatic perimeter further includes manual means for the operation of the signal application means.

The above and other objects and features of the present invention will become apparent from the following description of the preferred embodiment with reference to the accompanying drawings.

BRIEF DESCRIPTION OF THE DRAWINGS

FIGS. 3a & 3b comprise a flow chart showing overall operations of the aforementioned embodiment.

DESCRIPTION OF THE PREFERRED EMBODIMENTS

Figure 1:
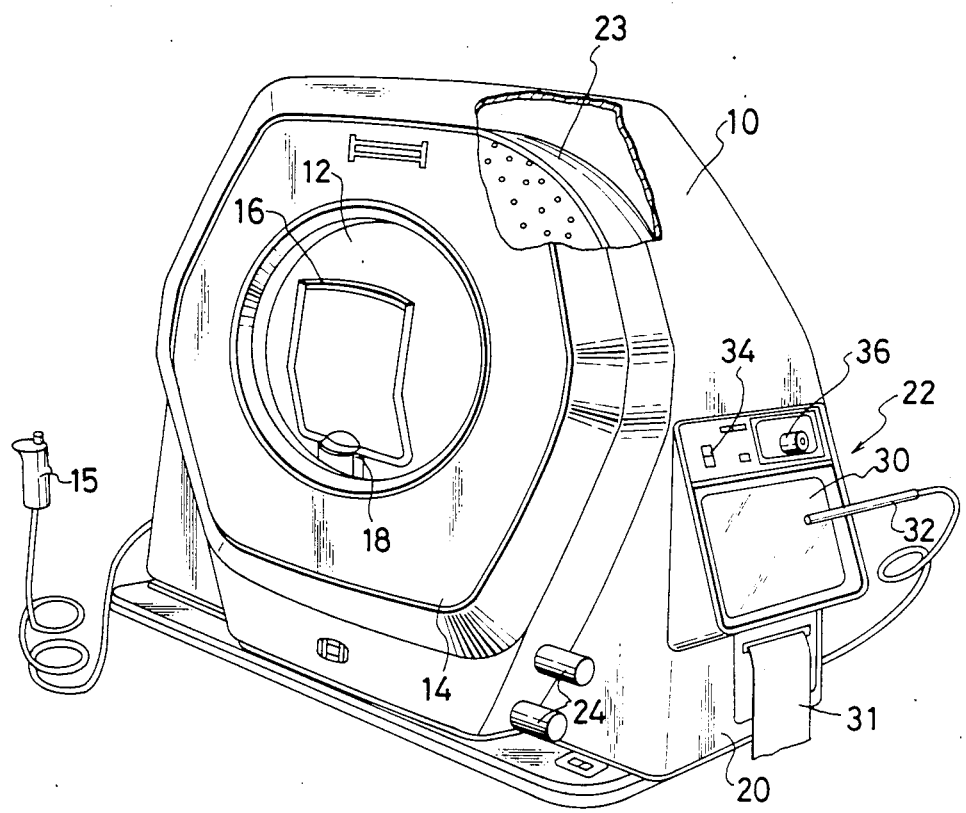
FIG. 1 is a perspective view showing the automatic perimeter in accordance with one embodiment of the present invention.

Referring now to the drawings, there is shown an automatic hemispherical perimeter in which the present invention is embodied. The automatic perimeter shown in FIG. 1 includes a housing 10, a panel 14 mounted on the housing 10 at its front side and having an opening 12 through which a patient's head goes in, a preception switch 15 operated by the patient, a front support 16 and a chin-rest 18 adjustably mounted in the housing 10 for fixing a patient's face, and a control and display apparatus 22 as described hereinafter. There are provided hand grips 24 for horizontally and vertically adjusting the front support 16 and the chin-rest 18 on the housing 10 at its lower side. There is also provided a hemispherical screen 23 in the housing 10 as directed against the opening 12.

The screen 23 has a plurality of light-emitting diodes as abbreviated to LED which are arranged on its whole inner surface in such a manner that they form a matrix to generate a plurality of stimuli and a fixation electroluminescence diode provided at the center of its inner surface for fixing a sight axis of the patient.

The control and display apparatus 22 includes a TV monitor 30, a light pen 32, a printer 31 located under the monitor 30, a control switch 34 located over the monitor 30, and a telescope 36 positioned over the monitor 30 for checking the fixation of the sight axis. The monitor 30 displays the kind, size, brightness and distribution of the stimuli, and different control commands as mentioned hereafter.

The printer 31 prints a result of the examination of eyesight. The telescope 36 is constituted to enable the operator to observe a front portion of the patient's eyes through an orifice located at substantially the same position as the fixation diode so as to enable the operator to check whether or not the sight axis is fixed to the fixation diode.

In the aforementioned perimeter, the patient's face is rested on the front support 16 and the chin-rest 18, and they are adjusted by the hand grips 24 so that the patient's eye to be measured is positioned at the center of the hemisphere of the screen 23. Subsequently, the fixation diode is lit to make the sight axis fix on the fixation diode, and each stimulus is successively presented on the screen 23 to examine the eyesight while the fixation of the sight axis is being checked through the telescope 36. The patient presses a button of the perception switch 15 when he perceives the stimulus, so that a response memory means as positioned hereafter memorizes the perception in relation to the condition in which the perceived stimulus is presented. The condition of the patient's eyesight is obtained by collecting the perceptions and the stimulus presentation conditions as memorized above.

The control commands adopted in the perimeter are as follows:

(1) To select examination program, such as a screening program to examine the whole of the sight field by using screened stimuli, or a meridional program to examine meridional directions. One of them is selected by the light pen 32 before the presentation.

(2) To determine main characteristics of the stimuli such as luminance, presentation time, and interval of presentation. These are given by the light pen 32 before the presentation.

(3) To carry out the examination program as selected. This is given by the light pen 32 or the control switch 34.

(4) To stop executing the examination program. This is given by the control switch 34 during performance of the examination program.

(5) To carry out the examination program from its stopped presentation step after the performance of the examination is interrupted. This is always given by the light pen 32 and given by the control switch 34 during interruption of performance of the examination program.

(6) To print a result of the examination. This is given by the light pen 32 and given by the control switch after the examination is completed.

Figure 2:
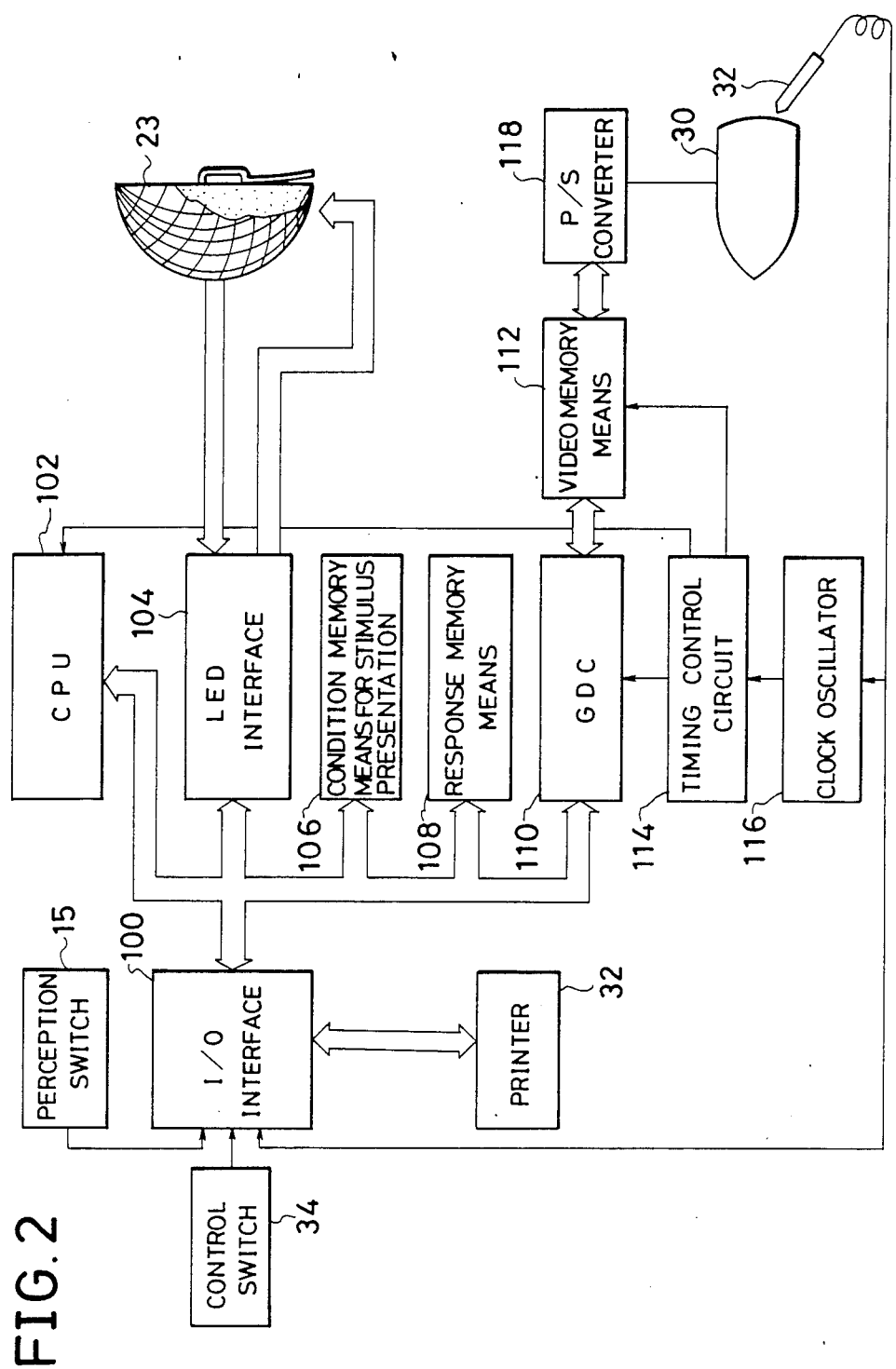
FIG. 2 is a block diagram of the control system adopted in the embodiment shown in FIG. 1.

A control system of the perimeter, as shown in FIG. 2, includes an input/output interface (called "I/O interface" hereafter) 100 having an input connected with the perception switch 15, the control switch 34 and the light pen 32. The I/O interface 100 has also a terminal connected with a central processing unit as abbreviated to CPU 102, a LED matrix interface (called "LED interface" hereafter) 104, condition memory means for stimuli presentation 106, the response memory means 108, a graphic display controller abbreviated to GDC 110 and a printer 32, and the I/O interface 100 functions to convert signals taken through the input into those proper for functions of the aforementioned internal elements and printing carried out by the printer 32.

The CPU 102 has an input connected with the LED interface 104, the condition memory means 106, the response memory means 108 and the GDC 110, and functions to perform main control of the perimeter as mentioned hereafter.

The LED interface 104 has a matrix composed of at least two transistor arrays to light the LED under a predetermined stimulus presentation condition taken from the CPU 102. The condition memory means 106 memorizes the stimulus presentation condition and the characteristics of the stimuli. The response memory means 108 memorizes the presentation conditions of the presented stimuli when the patient depresses the button of the perception switch 15 in accordance with his perception of the stimulus.

The GDC 110 takes a stimulus presentation signal, selected examination program signals, a position signal of the light stimulus and the response signal from the I/O interface 100, and functions to produce image signals which display information of said signals on the monitor 30. The GDC 110 has an output connected with a video memory means 112 and applies the image signals to the video memory 112. A timing control circuit 114 has an input connected with a clock oscillator 116 and an output connected with the CPU 102, the GDC 110 and the video memory 112, and functions to produce predetermined timing signals in accordance with clock signals taken from the clock oscillator 116. The timing signals are applied to the CPU 102, the GDC 110 and the video memory 112. A parallel-serial converter (called "P/S converter" hereafter) 118 has an input connected with the video memory 112 and an output connected with the monitor 30, and carries out parallel-serial conversion to convert parallel digital signals taken from the video memory 112 into serial video signals applied to the monitor 30.

Referring now to FIG. 3, there is shown a function of the perimeter controlled by the CPU 102. At first, the operator selects the examination program and determines the characteristics of the stimuli by the light pen 32. The control switch indicated as "CSW" in FIG. 3 generates a plurality of preselected command signals of which one of such preselected signals is produced at a time. At this time the control switch 34 is adapted to generate a command signal of "examination start" when it is turned on.

The operator has the patient put his face to the opening 12 so that the patient's eye to be examined is located at the center of the screen 23 by adjusting the hand grips 24. The patient is further asked to fix his sight axis to the fixation electroluminescent diode. After the operator confirms that the sight axis is fixed to the fixation diode through the telescope 36, the operator turns the control switch 34 on.

The CPU 102 monitors the control switch 34. When the control switch 34 is not turned on, the CPU 102 continues to judge the condition of the control switch 34 until the control switch 34 is turned on. When the control switch 34 is turned on, it has a second function different from the first one to generate a command signal of stimulus presentation stop. The LEDs on the inner surface of the screen 23 are individually lit through the LED interfaces 104 under the examination program and the characteristics of stimuli as selected above, so that the stimuli are presented to the patient. The patient turns the perception switch 15 on when he perceives the stimulus and the perception signals taken from the perception switch 15 are applied to the response memory means 108 so that the means 108 memorizes the preception signals.

The control switch 34 is monitored to determine whether or not it is turned on. If the control switch 34 is not turned on, the CPU 102 determines whether the stimulus presentation step to be carried out still remains. When the stimuli presentation step remains, the stimulus presentation condition is advanced by a step and the function of the CPU 102 is returned to the step where the function of the control switch 34 is changed to generate the command signal of "stimulus presentation stop". When all of the stimulus presentation steps are completed, the control switch 34 is used to generate a command signal of output. Then another determination is made as to whether the control switch 34 is turned on.

If the control switch 34 is not turned on, the CPU 102 continues to judge the condition of the control switch 34 until the control switch 34 is turned on. If the control switch 34 is turned on, namely, the command signal of "output" is generated, the examination signals memorized in the response memory means are converted into image signals through the GDC 110 to display the resulting value of examination by the monitor 30, and transferred to the I/O interface 100 to print out the resulting value of the examination. Then, the control switch 34 generates a command signal of "reset" when it is turned on, and it is determined whether or not the control switch 34 is turned on. If the control switch 34 is turned on, the examination program being performed is reset and the function of the CPU 102 is returned to the step for selecting the examination program and determining the characteristics of the stimuli. If the control switch 34 is not turned on, the judgement is made as to whether or not a power switch (not shown in Figures) is turned off. When the power switch is turned off, the examination is then completed. When the power switch is not turned off, the CPU 102 continues to judge the condition of the control switch 34 until the power switch is turned off.

On the other hand, when the operator finds that the sight axis of the patient is not fixed to the fixation electroluminescence diode during the step of the stimulus presentation, the operator turns the control switch 34 on and the control switch 34 generates a command signal to interrupt the stimulus presentation. Thereafter, the control switch 34 generates a command signal to restart the stimulus presentation when it is turned on. Then, the judgement is made as to whether or not a command signal of "examination stop" is supplied by the light pen 32. If the command signal of examination stop is supplied, the function of the CPU 102 is advanced to the step where the control switch 34 is used as a generation of the command signal of "output". If the command signal of "examination stop" is not supplied, the judgement is made on whether the control switch 34 is turned on or not.

When the control switch 34 is not turned on, the function of the CPU 102 is returned to the step determining whether or not the command signal of examination stop is supplied. While, when the control switch 34 is turned on, the data in response to the latest two presentations of the stimuli are canceled from the memory in the response memory means 108 and the stimulus presentation is returned by two steps. Then, the function of the CPU 102 is returned to the step where the control switch 34 generates the command signal of "stimulus presentation step".

The aforementioned flow-chart of the function of the CPU 102 is constituted as centering around the function of the control switch 34, and therefore it should be noted that the command signals of "output" and "reset" are always generated by the light pen 32 though they are generated by the control switch 34 in the predetermined condition as described above.

The invention has thus been shown and described with reference to a specific embodiment of the hemispherical perimeter having a plurality of stimuli of LEDs, however the invention is also possible to be adapted to a projection-type perimeter and a plane perimeter, and therefore it should be noted that the invention is in no way limited to the details of the illustrated embodiment but changes and modifications can be made within the scope of the appended claims.

We claim:

1. An automatic perimeter comprising stimulus presentation means for presenting stimuli to a patient, presentation condition memory means for memorizing a plurality of presentation conditions, control means for controlling the stimulus presentation means so as to present the stimuli in accordance with the presention conditions memorized in the presentation condition memory means, response means operated by the patient for supplying perception signals responding to presented stimuli, response signal memory means for memorizing the perception signals in relation to the presentation condition thereof, output means for supplying output of the perception signals memorized in the response signal memory means, first input means for applying a plurality of first command signals to the control means, second input means adapted to cooperate with said first input means to supply second command signals which are to be applied to the control means, and function change means for changing the command signals generated by the second input means in response to the stimulus presentation condition controlled by the control means.

2. An automatic perimeter in accordance with claim 1 in which the first input means comprises a cathode-ray tube displaying a plurality of control commands and a light pen.

3. An automatic perimeter in accordance with claim 1 in which the second input means comprises a manual switch.

4. An automatic perimeter in accordance with claim 1 in which the second input means includes means to start examination before beginning presentation of stimuli and to stop and restart the presentation of stimuli.

5. An automatic perimeter comprising stimulus presentation means for presenting stimuli in a plurality of conditions, presentation condition memory means for memorizing a presentation condition in a plurality of steps, control means for supplying presentation control signals to the stimulus presentation means in accordance with the presentation condition memorized in the presentation condition memory means, response means operated by a patient for supplying perception signals responding to presented stimuli, response signal memory means for memorizing the perception signals in relation to the presentation condition thereof, output means for supplying output of the perception signals memorized in the response signal memory means, and signal application means for supplying presentation stop signals and presentation restart signals to the control means and supplying at least one of said signals to the response signal memory means, said control means being arranged to stop supplying the presentation control signal to the stimulus presentation means on taking the presentation control signal, to return a predetermined number of presentation steps and to restart supplying the presentation control signals on taking the presentation restart signal, and means responsive to said at least one of said presentation stop and presentation restart signals for cancelling the memorized perception signals responsive to the returned presentation steps when the response memory means receives either the presentation stop signal of the presentation restart signal.

6. An automatic perimeter in accordance with claim 5 which further includes manual means for operating the signal application means.

* * * * *